(12) United States Patent
Minion

(10) Patent No.: US 12,150,876 B2
(45) Date of Patent: Nov. 26, 2024

(54) GUIDING SHEATH SYSTEM AND METHOD OF DELIVERING AN ENDOVASCULAR DEVICE USING THE SAME

(71) Applicant: University of Kentucky Research Foundation, Lexington, KY (US)

(72) Inventor: David J Minion, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 678 days.

(21) Appl. No.: 17/242,989

(22) Filed: Apr. 28, 2021

(65) Prior Publication Data

US 2021/0330481 A1 Oct. 28, 2021

Related U.S. Application Data

(60) Provisional application No. 63/016,494, filed on Apr. 28, 2020.

(51) Int. Cl.
*A61F 2/966* (2013.01)
*A61M 25/06* (2006.01)

(52) U.S. Cl.
CPC ......... *A61F 2/966* (2013.01); *A61M 25/0662* (2013.01)

(58) Field of Classification Search
CPC ............... A61F 2/966; A61M 25/0662; A61M 25/0147
See application file for complete search history.

(56) References Cited

U.S. PATENT DOCUMENTS

| | | | | |
|---|---|---|---|---|
| 6,071,274 | A * | 6/2000 | Thompson | A61M 25/0144 604/533 |
| 6,332,880 | B1 * | 12/2001 | Yang | A61B 18/1492 604/95.04 |
| 10,646,340 | B2 * | 5/2020 | Manash | A61M 25/0138 |

* cited by examiner

*Primary Examiner* — Julian W Woo
(74) *Attorney, Agent, or Firm* — Stites & Harbison PLLC; James R. Hayne

(57) ABSTRACT

A guiding sheath system includes a first sheath having a proximal end and a distal end, an extension member connected to the distal end of the first sheath, the extension member terminating in a distal end, a second sheath extending through the first sheath, the second sheath having a proximal end and a distal end, and a cap connected to the distal end of the extension member and the distal end of the second sheath. Upon advancing the second sheath through the first sheath, the cap restrains the distal end of the second sheath and the cap deflects relative to the first sheath thereby causing a portion of the second sheath protruding from the first sheath to bend into a curve with the distal end of the second sheath at a vector different from a vector of the first sheath.

6 Claims, 9 Drawing Sheets

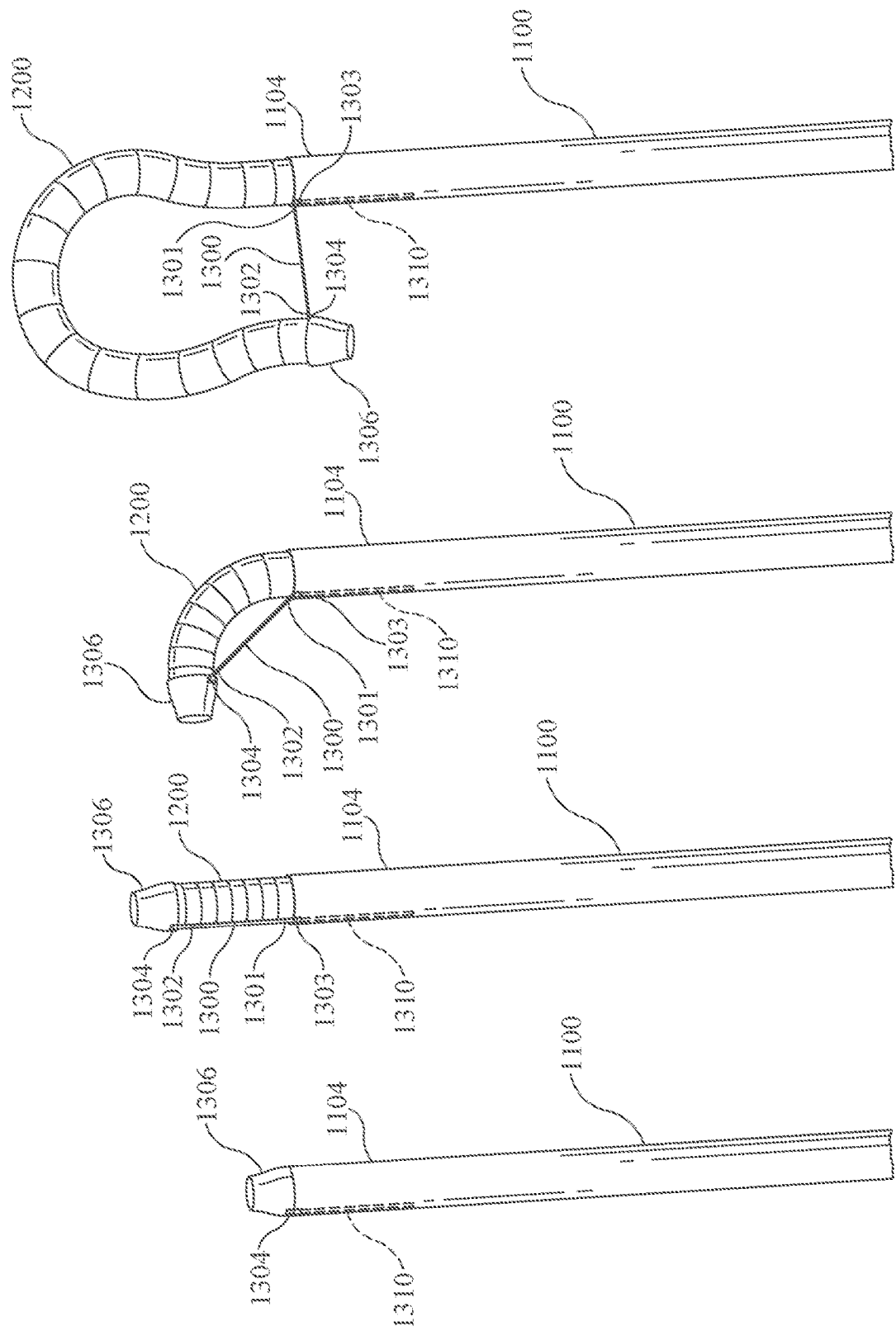

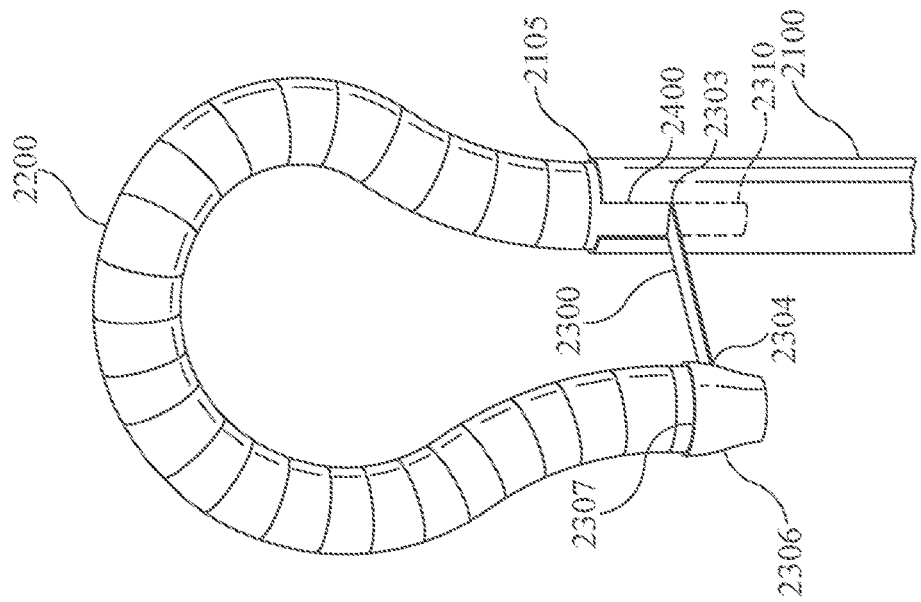
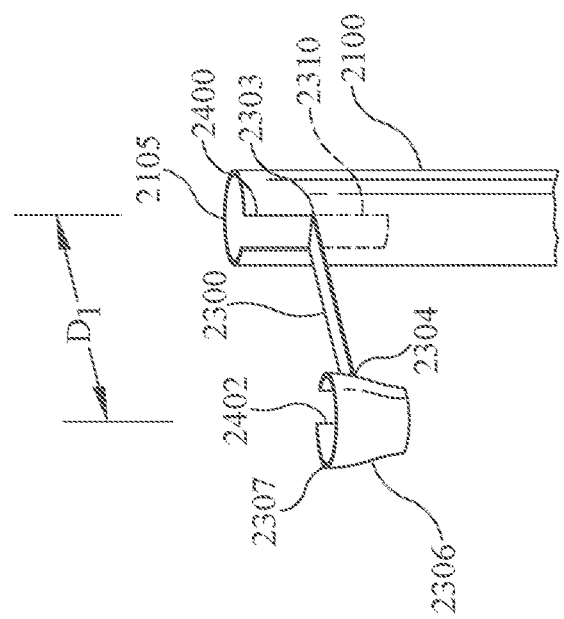
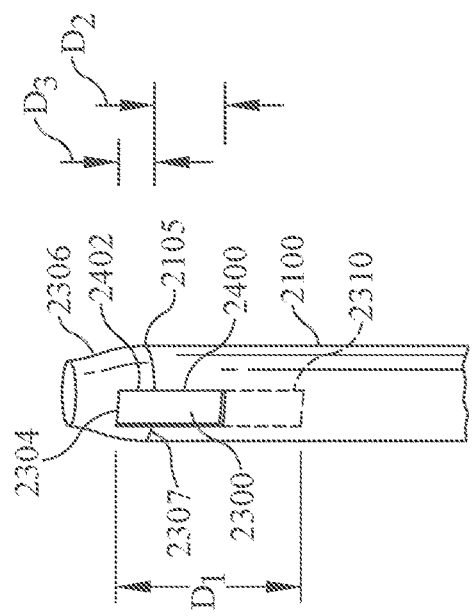
Fig. 3C
Fig. 3B
Fig. 3A

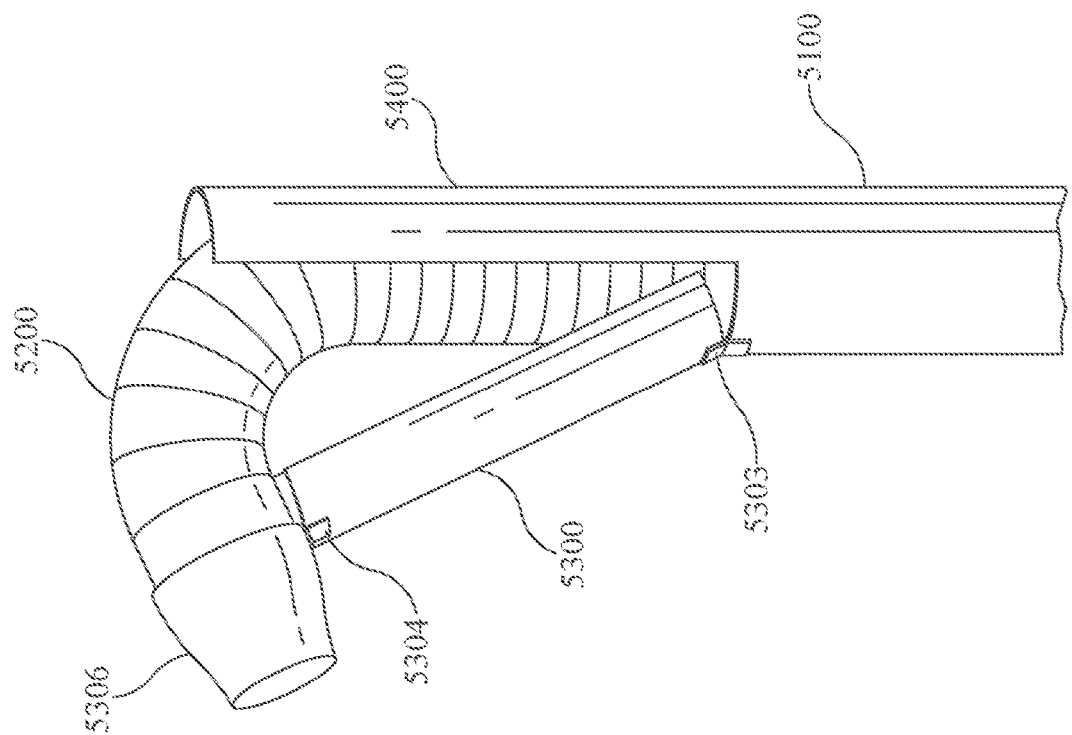
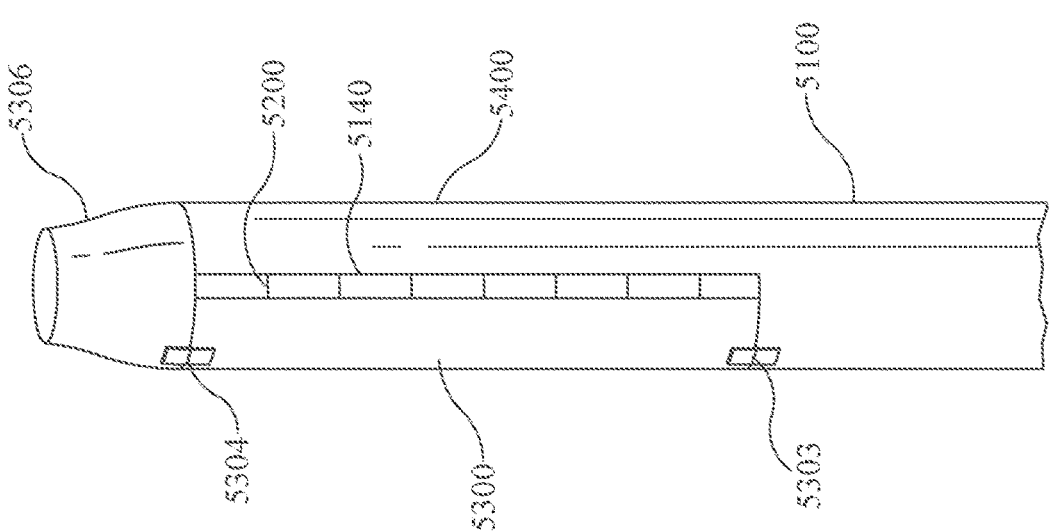

GUIDING SHEATH SYSTEM AND METHOD OF DELIVERING AN ENDOVASCULAR DEVICE USING THE SAME

CROSS-REFERENCE TO RELATED APPLICATIONS

The present application claims priority to U.S. Provisional Patent Application Ser. No. 63/016,494 filed on Apr. 28, 2020, the entire disclosures of which are incorporated herein by reference.

TECHNICAL FIELD

The present invention relates to guiding sheaths used to introduce and deliver endovascular devices to their intended destination in the vascular system of a patient. In particular, the invention relates to a guiding sheath system in which a hinge, or hinge-like, connection at the end of the sheath directs, and firmly maintains, the end of the sheath in a vector that is different than that of the remainder of the sheath.

BACKGROUND OF THE INVENTION

Guiding sheaths, or guiding catheters, are tube-like devices designed to be placed with the distal end of the sheath position within the vasculature and the proximal end of the sheath kept extracorporeal, thereby allowing introduction of endoluminal devices into the vasculature through the sheath. In some cases, these sheaths are constructed of different shapes to facilitate delivery of devices in angulated anatomy. However, these shaped must still have the flexibility to be straightened during their initial placement into blood vessels and therefore often lack the rigidity to maintain their shape during tracking of larger or stiffer endoluminal devices in challenging anatomy.

SUMMARY OF THE INVENTION

The present invention is a guiding sheath system with a hinge-like connection at the end of the sheath which directs, and firmly maintains, the end of the sheath in a vector that is different than that of the remainder of the sheath.

One exemplary guiding sheath system made in accordance with the present invention includes a first, or outer, sheath having a proximal end and a distal end and a second, or inner, sheath extending through the first sheath, the second sheath having a proximal end and a distal end. A first extension member is connected to the distal end of the first sheath with the first extension member terminating in a distal end, and a cap connected to the distal end of the extension member and the distal end of the second sheath. Upon advancing the second sheath through the first sheath, the cap restrains the distal end of the second sheath and the cap deflects relative to the first sheath thereby causing a portion of the second sheath protruding from the first sheath to bend into a curve with the distal end of the second sheath at a vector different from a vector of the first sheath.

In some embodiments, the first extension member is fixedly connected to the distal end of the first sheath with the extension member extending away from the distal end of the first sheath at a vector the same as the vector of the first sheath.

In some embodiments, the first extension member is configured to deflect relative to the first sheath, such that, upon advancing the second sheath through the first sheath, the extension member extends at a vector different from the vector of the first sheath.

In some embodiments, a second extension member is connected to the distal end of the first sheath with the extension member terminating in a distal end.

In some embodiments, the second extension member is shorter than the first extension member.

In some embodiments, the second extension member is substantially the same length as the first extension member.

In some embodiments, the second extension member is configured to deflect relative to the first sheath, such that, upon advancing the second sheath through the first sheath, the second extension member extends at a vector different from the vector of the first sheath.

In some embodiments, the first extension member is pivotally connected to the distal end of the first sheath.

In some embodiments, the second extension member is pivotally connected to the distal end of the first sheath.

In some embodiments, the first extension member is slidably connected to the distal end of the first sheath such that, when the first extension member is in a retracted position, the cap is positioned adjacent to the distal end of the first sheath and when the first extension member is in an extended position, the first extension member extends from the distal end of the first sheath such that the cap is positioned a distance away from the distal end of the first sheath.

In some embodiments, upon advancing the second sheath through the first sheath, the first extension member is moved into the extended position and the extension member deflects relative to the first sheath, thereby causing the extension member to extend at the vector different from the vector of the first sheath In some embodiments, the distal end of the first sheath, the cap, or both the distal end of the first sheath and the cap define a cutout, and the extension member passes through the cutout when the extension member deflects relative to the first sheath.

According to the methods of the present invention, an exemplary guiding sheath system, such as one of the systems described above, is first provided and inserted into the vasculature of a patient and advanced through the patient's vasculature until the cap is at a predetermined location within the vasculature. The second sheath is advanced relative to the first sheath, such that the cap restrains the distal end of the second sheath and the cap deflects relative to the first sheath thereby causing a portion of the second sheath protruding from the first sheath to bend into a curve with the distal end of the second sheath at a vector different from a vector of the first sheath. In particular, the distal end of the second sheath is positioned so that the opening at the distal end of the inner sheath is pointing towards the opening to the branching vessel while the distal end of the first sheath is substantially aligned with the primary vessel. An endovascular device is then advanced through the second sheath to a position forward of the distal end of the second sheath along the vector of the distal end of the second sheath.

Further features and advantages of the present invention will become evident to those of ordinary skill in the art after a study of the description, figures, and non-limiting examples in this document.

DESCRIPTION OF THE DRAWINGS

FIG. 2A is a perspective view of another guiding sheath system made in accordance with the present invention with an inner sheath in a retracted position relative to an outer sheath;

FIG. 2B is a perspective view of the guiding sheath system of FIG. 2A with the inner sheath partially advanced through the outer sheath and an extension member fully extended;

FIG. 2C is a perspective view of the guiding sheath system of FIG. 2A with the inner sheath further advanced through the outer sheath and the extension member deflected;

FIG. 2D is a perspective view of the guiding sheath system of FIG. 2A with the inner sheath further advanced through the outer sheath and the extension member further deflected;

FIG. 3A is a perspective view of another guiding sheath system made in accordance with the present invention with an inner sheath in a retracted position relative to an outer sheath;

FIG. 3B is a perspective view of the outer sheath of the guiding sheath system of FIG. 3A with an extension member fully extended and deflected;

FIG. 3C is a perspective view of the guiding sheath system of FIG. 3A with the inner sheath advanced through the outer sheath and the extension member fully extended and deflected;

FIG. 6A is a perspective view of another guiding sheath system made in accordance with the present invention with an inner sheath in a retracted position relative to an outer sheath;

FIG. 6B is a perspective view of the guiding sheath system of FIG. 6A with the inner sheath partially advanced through the outer sheath and a first extension member deflected;

DESCRIPTION OF THE INVENTION

The invention relates to the design of guiding sheaths, or guiding catheters, used to introduce and deliver endovascular devices (such as stents, grafts, balloons, etc.) to their intended destination in the vascular system of a patient. More specifically, the invention relates to a guiding sheath system with a hinge-like connection at the end of the sheath which directs, and firmly maintains, the end of the sheath in a vector that is different than that of the remainder of the sheath.

Figure 1C:
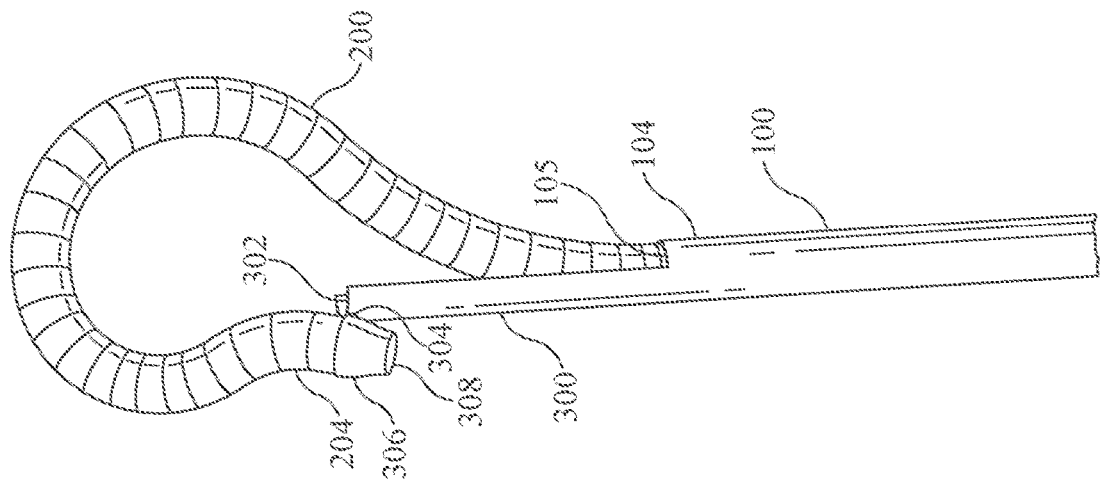
FIG. 1C is a perspective view of the guiding sheath system of FIG. 1A with the inner sheath further advanced through the outer sheath.
Figure 1B:
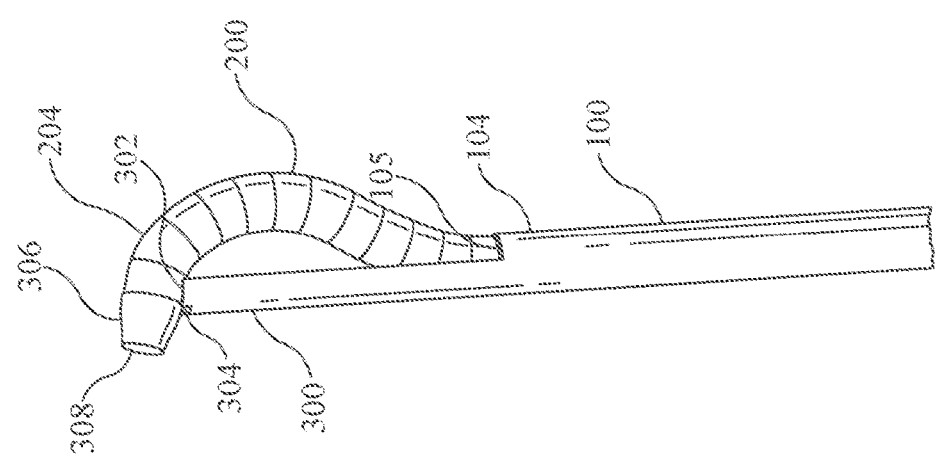
FIG. 1B is a perspective view of the guiding sheath system of FIG. 1A with the inner sheath partially advanced through the outer sheath.
Figure 1A:
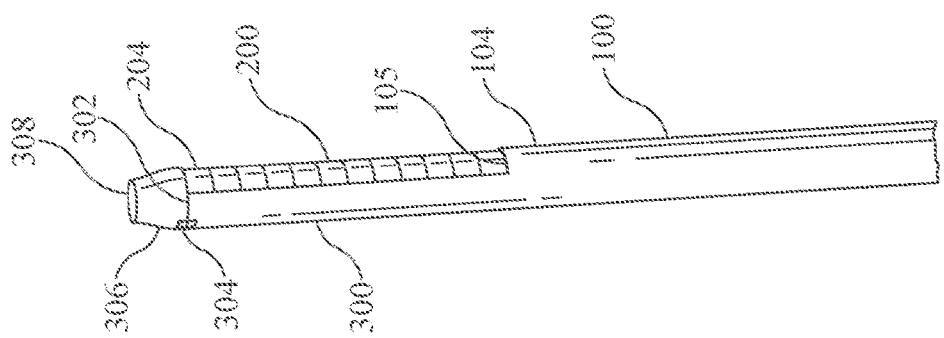
FIG. 1A is a perspective view of a guiding sheath system made in accordance with the present invention with an inner sheath in a retracted position relative to an outer sheath.

Referring first to FIGS. 1A-1C, an exemplary guiding sheath system made in accordance with the present invention includes a first, or outer, sheath 100 having a proximal end (not shown) and a distal end 104, an extension member 300 operably connected to and projecting from the distal end 104 of the outer sheath 100 so as to terminate in a distal end 302, and a second, or inner, sheath 200 having a proximal end (not shown) and a distal end 204. As used herein, the terms "distal" and "proximal" are used in relation to an operator. The distal end is sometimes referred to as the "tip" of the device and the proximal end is sometimes referred to as the "hub."

With respect to the sheaths 100, 200 in particular, the outer sheath 100 is in the form of a hollow tube having an opening at its proximal end which is operably connected to an opening 105 (e.g., distal edge) at its distal end 104. Similarly, the inner sheath 200 is also in the form of a hollow tube having an opening at its proximal end which is operably connected to an opening at its distal end 204. Furthermore, although not shown, in some preferred embodiments, one or more of the outer sheath 100 and the inner sheath 200 include a hemostatic valve at their respective proximal ends.

The inner sheath 200 is sized to fit within the outer sheath 100 with the proximal end of the inner sheath 200 extending out of the proximal end of the outer sheath 100 and the distal end 204 of the inner sheath 200 extending out of the distal end 104 of the outer sheath 100.

A cap 306 is positioned at the distal end 302 of the extension member 300 and operably connected to the distal end 302 of the extension member 300 such that the cap 306 can deflect, or pivot, around a connection point between the extension member 300 and the cap 306. In other words, the cap 306 is connected to the extension member with a true hinge, a functional hinge, or the like (i.e., hinge 304). The inner sheath 200 extends through the outer sheath 100 with the distal end 204 of the inner sheath 200 also operably connected to the cap 306. In this way, an opening 308 at the end of cap 306 leads to the interior of the inner sheath 200.

In some embodiments, the cap 306 is a separate member affixed to both the outer sheath 100 and the inner sheath 200. For example, a suture, or other similar means of connection, may be used to affix the cap 306 to the extension member 300 in a manner to allow the cap 306 to deflect, or pivot, relative to the extension member 300. The distal end 204 of the inner sheath 200 may be affixed to the cap 306 with a similar means of connection, but in such a manner as to keep the inner sheath 200 securely connected to the cap 306. In some other embodiments, the cap 306 is formed as an integral portion of the inner sheath 200 which is then affixed to the outer sheath 100, i.e., with or through formation of the hinge 304. In some other embodiments, the cap 306 is formed from part of the outer sheath 100. In particular, in some preferred embodiments, the outer sheath 100, the extension member 300, and the cap 306 are each formed from a unitary cylindrical sheath. Part of this original cylindrical sheath is cut away to leave the extension member 300 extending from the outer sheath 100 and then a cut is made partially around the sheath at the distal end 302 of the extension member 300 leaving the hinge 304 in place. Before or after these cuts are made, the distal end 204 of the inner sheath 200 can be affixed to the distal end of the original cylindrical sheath thereby forming the cap 306.

In any event, in some embodiments the cap 306 is configured to provide a rounded leading edge of the guiding sheath system. This smooth transition facilitates inserting and advancing the system through the vasculature, as further discussed below.

It is contemplated that, in some embodiments of the present invention, the cap can be absent without departing from the spirit and scope of the present invention. For example, a distal end of the inner sheath can, in some embodiments, be directly affixed to the extension member by means which would operate in a hinge-like manner.

Referring now specifically to FIGS. 1B and 1C, the guiding sheath system of the present invention is configured such that the inner sheath 200 can be advanced relative to (e.g., through) the outer sheath 100. In particular, as shown in FIG. 1B, as the inner sheath 200 is partially advanced relative to the outer sheath 100, the cap 306 restrains the distal end 204 of the inner sheath 200 and the cap 306 begins to deflect, or pivot, relative to the outer sheath 100 around the hinge 304.

As shown in FIGS. 1B and 1C, as the inner sheath 200 is advanced relative to the outer sheath 100, the portion of the inner sheath 200 protruding from the outer sheath 100 bends into a curve. To this end, the inner sheath 200 preferably is made of a woven or braided material, for example, nitinol, which prevents kinks from forming along the length of the inner sheath 200. Instead, the woven body of the inner sheath 200 promotes a gradual curve in the inner sheath 200, such as is shown in FIGS. 1B and 1C. In some embodiments, the outer sheath 100 is likewise made of a woven or braided material, for example, nitinol.

Referring still to FIGS. 1A-1C, the vector of the distal end 204 of the inner sheath 200 (i.e., the direction of the opening 308 of the cap 306) can be controlled by advancing the inner sheath 200 relative to the outer sheath 100. In FIG. 1A, the inner sheath 200 is substantially straight and the distal end 204 of the inner sheath 200 is directed in a vector that is substantially the same as the vector of the remainder of the inner sheath 200 (i.e., the portion of the inner sheath 200 still positioned within the outer sheath 100). In other words, the opening 308 of the cap 306 points in substantially the same direction as the opening 105 at the distal end 104 of the outer sheath 100. In FIG. 1B, the distal end 204 of the inner sheath 200 is directed in a vector that is about 90° different than the vector of the remainder of the inner sheath 200. In other words, the opening 308 of the cap 306 points in a direction different from the direction as the opening 105 at the distal end 104 of the outer sheath 100. In FIG. 1C, the distal end 204 of the inner sheath 200 is pointing substantially 180° opposite the remainder of the inner sheath 200. Accordingly, the distal end 204 of the inner sheath 200 can therefore be manipulated into various directions, including retrograde. Once again, the woven body of the inner sheath 200 promotes a gradual curve in the inner sheath 200 and prevents kinks from forming along the length of the inner sheath 200.

Advantageously, the hinge 304 between the extension member 300 and the cap 306 firmly maintains the position of the distal end 204 of the inner sheath 200 relative to the distal end 104 of the outer sheath 100, allowing for rotation of the device about the main axis of the outer sheath 100, even when the inner sheath 200 is extended, so as to position the opening 308 of the cap 306 in line with a targeted branching vasculature, as further discussed below.

In the embodiment shown in FIGS. 1A-1C, the extension member 300 is fixedly connected to the distal end 104 of the outer sheath 100 with the extension member 300 extending away from the distal end 104 of outer sheath 100 at a vector the same as the vector of the outer sheath 100. Even as the inner sheath 200 is advanced and begins to curve, the extension member 300 remains pointing in essentially the same direction as the outer sheath 100.

However, in other embodiments, the extension member is configured to deflect relative to the outer sheath, such that upon advancing the inner sheath through the outer sheath the extension member extends at a vector different from the vector of the first sheath. Such deflection can be enabled by simply changing the stiffness of extension member 300 or by incorporating additional mechanisms.

For example, and referring now to FIGS. 2A-2D, in another exemplary system of the present invention, an outer sheath 1100, an inner sheath 1200, and a cap 1306 are provided which are similar to the outer sheath 100, inner sheath 200, and cap 306 described above with respect to FIGS. 1A-1C with similar components bearing similar reference numerals but advanced into the 1000s. In the embodiment shown in FIGS. 2A-2C, rather than an extension member fixedly projecting from the distal end 1104 of the outer sheath 1100, the extension member 1300 shown in FIGS. 2B-2D is slidably connected to the outer sheath 1100 such that the extension member 1300 is moveable between a retracted position (FIG. 2A) and an extended position (e.g., FIGS. 2B-2D). In the embodiment shown in FIGS. 2A-2D, when the extension member 1300 is in the retracted position (FIG. 2A), the extension member 1300 is housed within the outer sheath 1100, but in some embodiments, when the extension member 1300 is in the retracted position, the extension member 1300 may be housed outside of the outer sheath 1100.

As shown in FIG. 2A, a guide 1310, or other similar restraining feature, is provided in the outer sheath 1100 to house the extension member 1300 when retracted, but also direct the extension member 1300 as it is extended. In some embodiments, a flange, or other similar member is included at the proximal end 1301 of the extension member 1300 so as to stop travel of the extension member 1300 when fully extended, as shown, for example, in FIGS. 2B-D2. The particular means of housing and/or selectively restraining the extension member 1300 is not limited. Regardless, in some preferred embodiments, when the extension member 1300 is in the retracted position (FIG. 2A), the cap 1306 is positioned adjacent to the distal end 1104 of the outer sheath 1100.

As shown in FIGS. 2B-2D, when the extension member 1300 is in the extended position, the cap 1306 is positioned a distance away from the distal end 1104 of the outer sheath 1100. In the preferred embodiment shown in FIGS. 2A-2D, once the extension member 1300 is fully extended (shown in FIGS. 2B-2D), another hinge (functional hinge) 1303 at the proximal end 1301 of the extension member 1300 allows the extension member 1300 to deflect, or pivot, relative to the outer sheath 1100 in substantially the same manner as the hinge 1304 at the distal end 1302 of the extension member 1300 allows the cap 1306 to deflect, or pivot, relative to the extension member 1300.

Referring now to FIGS. 3A-3C, in yet another exemplary system of the present invention, an outer sheath 2100, an inner sheath 2200 (only shown in FIG. 3C), and a cap 2306 are provided which are similar to the outer sheath 1100, inner sheath 1200, and cap 1306 described above with respect to FIGS. 2A-2D with similar components bearing similar reference numerals but advanced into the 2000s. In the embodiment shown in FIGS. 3A-3C, rather than the proximal hinge 2303 allowing deflection of the extension member 2300 at the very distal end 2105 of the outer sheath 2100, the outer sheath 2100 defines a cutout 2400 which allows the extension member 2300 to deflect, or pivot, a distance away from the distal edge 2105 of the outer sheath 2100. The cap 2306 likewise defines a cutout 2402 which allows the extension member 2300 to deflect, or pivot, a distance away from the proximal end 2307 of the cap 2306.

In the embodiment shown in FIGS. 3A-3C, the extension member 2300 has a length, D1; the cutout 2400 in the outer sheath 2100 has a length, D2; and the cutout 2402 in the cap 2306 has a length, D3 such that the extension member 2300 is longer than the two cutouts combined (i.e., D1>D2+D3). As such, in this embodiment, a guide 2310 is still provided in the outer sheath 2100 to allow for the longitudinal travel of the extension member 2300. Once the extension member 2300 is fully extended, another hinge (functional hinge) 2303 at the proximal end of the extension member 2300 allows the extension member 2300 to deflect, or pivot, relative to the outer sheath 2100. Advantageously, the extension member 2300 passes through the cutouts 2400, 2402 to thereby allow for the extension member 2300 to deflect, or pivot, without requiring the extension member 2300 to extend as far out of the outer sheath 2100. Alternatively, the embodiment could be constructed without guide 2310 such that hinge 2303 is mechanically fixed at the proximal end of cutout 2400 (i.e., D1=D2+D3).

Figure 4B:
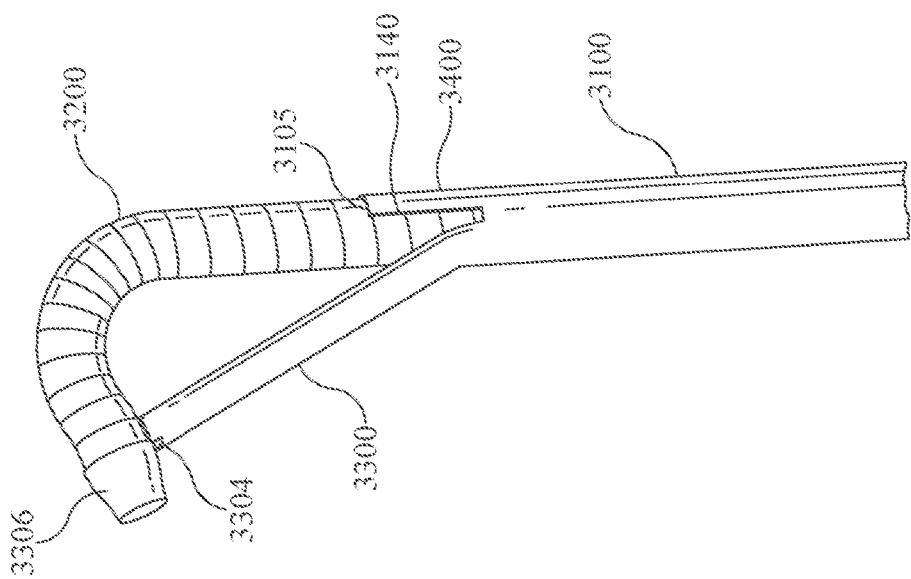
FIG. 4B is a perspective view of the guiding sheath system of FIG. 4A with the inner sheath partially advanced through the outer sheath with an extension member deflected.
Figure 4A:
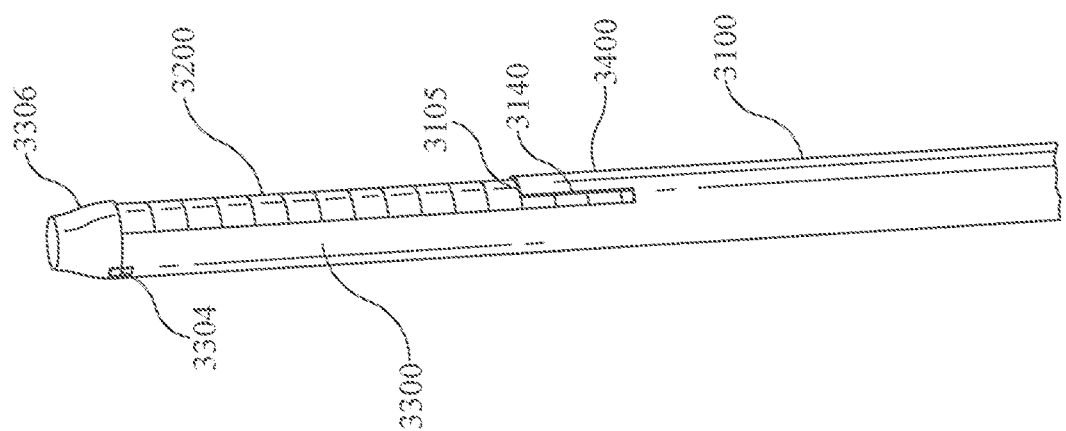
FIG. 4A is a perspective view of another guiding sheath system made in accordance with the present invention with an inner sheath in a retracted position relative to an outer sheath.

Referring now to FIGS. 4A and 4B, in yet another exemplary embodiment, an outer sheath 3100, an inner sheath 3200, and a cap 3306 are provided which are similar to the outer sheath 100, inner sheath 200, and cap 306 described above with respect to FIGS. 1A-1C with similar components bearing similar reference numerals but advanced into the 3000s. In the embodiment shown in FIGS. 4A and 4B, the outer sheath 3100 defines a slit 3140 which promotes deflection of the extension member 3300 itself relative to the outer sheath 3100 at the proximal end of the slit 3400. That is to say, as shown in FIG. 4B, as the inner sheath 3200 is advanced and begins to curve, in addition to the cap 3306 deflecting or pivoting relative to the extension member 3300 around the hinge 3304, the extension member 3300 deflects relative to the outer sheath 3100, such that the extension member 3300 extends at a vector different from the vector of the outer sheath 3100.

The embodiment shown in FIGS. 4A and 4B can also be characterized as having a first extension member 3300 connected to the distal end 3104 of the outer sheath 3100 and also a second extension member 3400 connected to the distal end 3104 of the outer sheath 3100 with the slit 3140 defined between the first extension member 3300 and the second extension member 3400. Similar to the first extension member 3300, the second extension member 3400 terminates in a distal end 3105.

In the embodiment shown in FIGS. 4A and 4B, the second extension member 3400 is shorter than the first extension member 3300, but the length of the first and second extension members is not limited and could include a length of zero (i.e., absence) for the second extension.

Figure 5B:
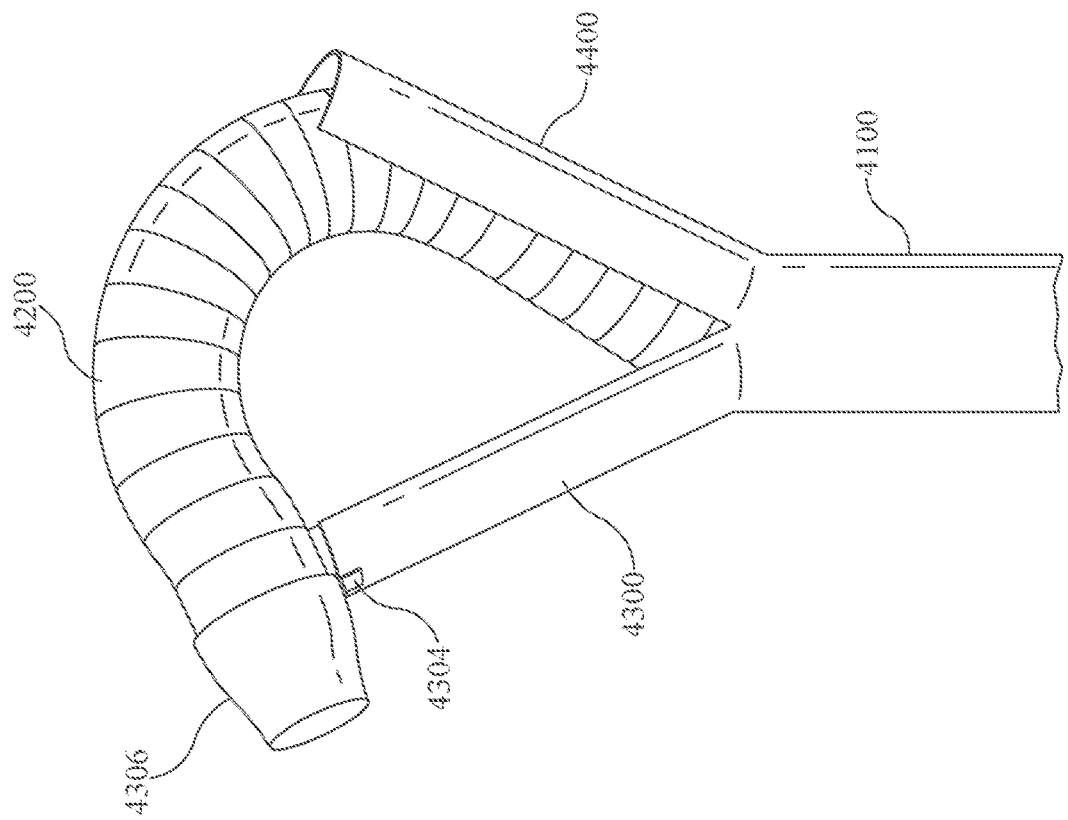
FIG. 5B is a perspective view of the guiding sheath system of FIG. 5A with the inner sheath partially advanced through the outer sheath, a first extension member deflected, and a second extension member deflected.
Figure 5A:
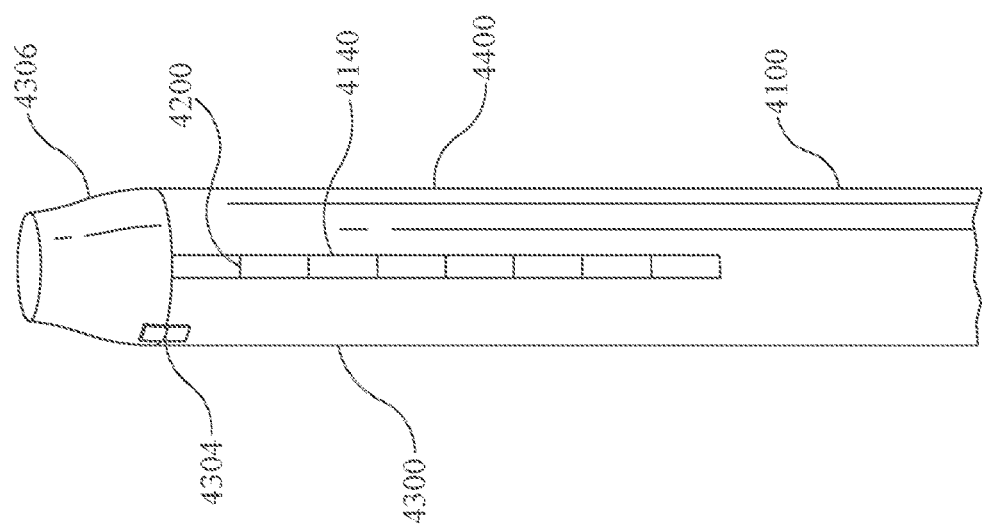
FIG. 5A is a perspective view of another guiding sheath system made in accordance with the present invention with an inner sheath in a retracted position relative to an outer sheath.

Referring now to FIGS. 5A and 5B, in yet another exemplary embodiment, an outer sheath 4100, an inner sheath 4200, and a cap 4306 are provided which are similar to the outer sheath 3100, inner sheath 3200, and cap 3306 described above with respect to FIGS. 4A and 4B with similar components bearing similar reference numerals but advanced into the 4000s. Specifically, a slit 4140 is defined between a first extension member 4300 and a second extension member 4400. However, in the embodiment shown in FIGS. 5A and 5B, the first extension member 4300 and the second extension member 4400 are substantially the same length.

According to this embodiment, as the inner sheath 4200 is advanced and begins to curve, in addition to the cap 4306 deflecting or pivoting relative to the first extension member 4300 around the hinge 4304, both the first extension member 4300 and the second extension member 4400 deflect relative to the outer sheath 4100, such that the first extension member 4300 and the second extension member 4400 each extend at vectors different from the vector of the outer sheath 4100.

Referring now to FIGS. 6A and 6B, in yet another exemplary embodiment, an outer sheath 5100, an inner sheath 5200, and a cap 5306 are provided which are similar to the outer sheath 4100, inner sheath 4200, and cap 4306 described above with respect to FIGS. 5A and 5B with similar components bearing similar reference numerals but advanced into the 5000s. Specifically, a slit 5140 is defined between a first extension member 5300 and a second extension member 5400 which are substantially the same length. In the embodiment shown in FIGS. 6A and 6B, in addition to the cap 5306 being operably connected to the first extension member 5300 with a hinge 5304 as discussed above, the first extension member 5300 is operably connected to the outer sheath 5100 with another hinge (functional hinge) 5303 which allows the first extension member 5300 to deflect, or pivot, relative to the outer sheath 5100.

According to this embodiment, as the inner sheath 5200 is advanced and begins to curve, it is contemplated that only the first extension member 5300 deflects relative to the outer sheath 5100, such that the first extension member 5300 extends at a vector different from the vector of the outer sheath 5100. By comparison, the second extension member 5400 is fixedly connected to the outer sheath 5100 and therefore remains pointing in essentially the same direction as the outer sheath 5100.

Figure 7B:
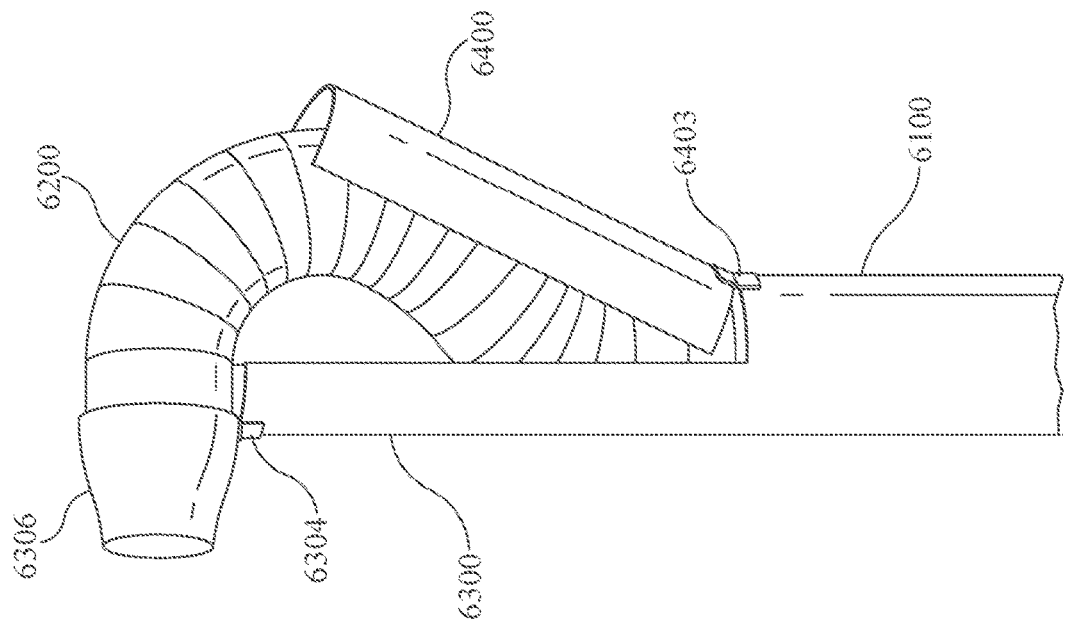
FIG. 7B is a perspective view of the guiding sheath system of FIG. 7A with the inner sheath partially advanced through the outer sheath and a second extension member deflected.
Figure 7A:
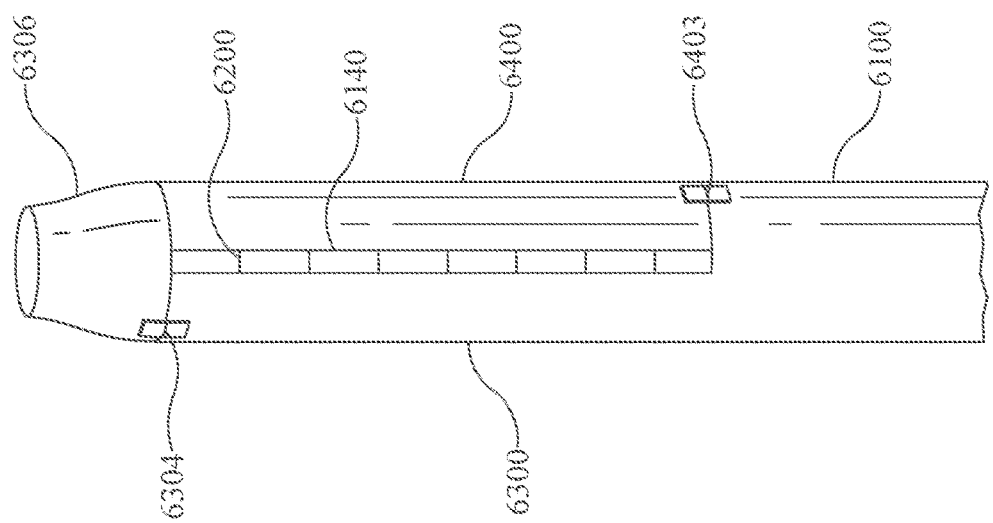
FIG. 7A is a perspective view of another guiding sheath system made in accordance with the present invention with an inner sheath in a retracted position relative to an outer sheath.

Referring now to FIGS. 7A and 7B, in yet another exemplary embodiment, an outer sheath 6100, an inner sheath 6200, and a cap 6306 are provided which are similar to the outer sheath 4100, inner sheath 4200, and cap 4306 described above with respect to FIGS. 5A and 5B with similar components bearing similar reference numerals but advanced into the 5000s. Specifically, a slit 6140 is defined between a first extension member 6300 and a second extension member 6400 which are substantially the same length. In the embodiment shown in FIGS. 7A and 7B, the second extension member 6400 is operably connected to the outer sheath 6100 with another hinge (functional hinge) 6403 which allows the second extension member 6400 to deflect, or pivot, relative to the outer sheath 6100.

According to this embodiment, as the inner sheath 6200 is advanced and begins to curve, in addition to the cap 6306 deflecting or pivoting relative to the first extension member 6300 around the hinge 6304, it is contemplated that only the second extension member 6400 deflects relative to the outer sheath 6100, such that the second extension member 6400 extends at a vector different from the vector of the outer sheath 6100. By comparison, the first extension member 6300 is fixedly connected to the outer sheath 6100 and therefore remains pointing in essentially the same direction as the outer sheath 6100.

Figure 8B:
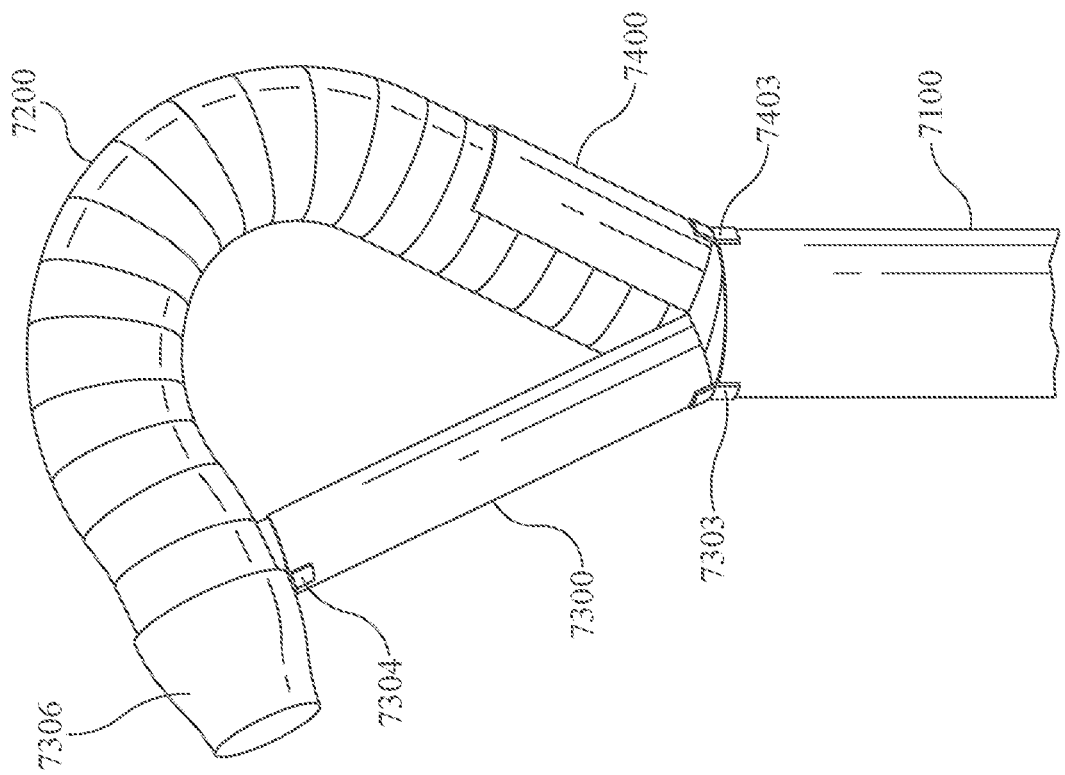
FIG. 8B is a perspective view of the guiding sheath system of FIG. 8A with the inner sheath partially advanced through the outer sheath, a first extension member deflected, and a second extension member deflected.
Figure 8A:
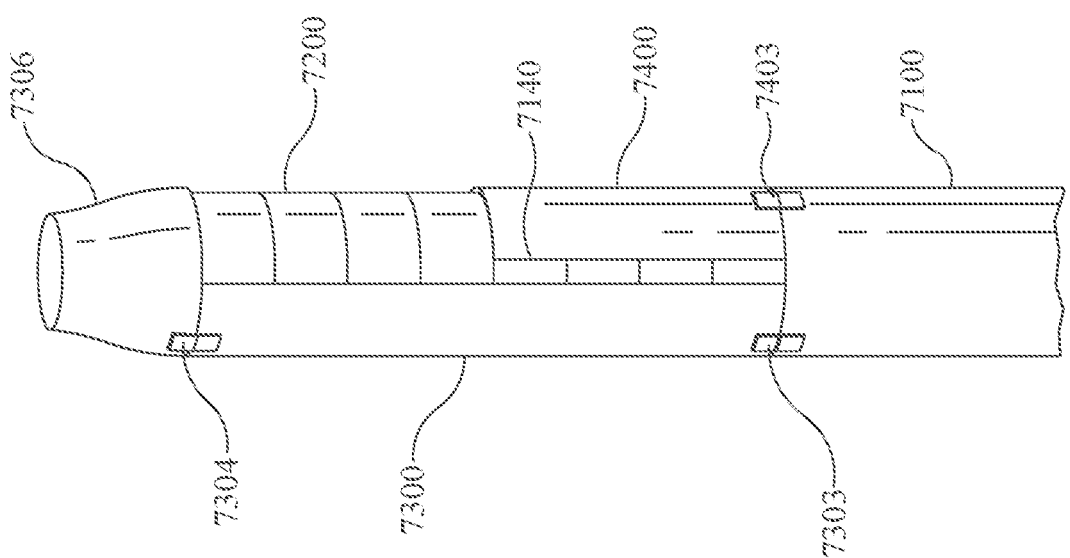
FIG. 8A is a perspective view of another guiding sheath system made in accordance with the present invention with an inner sheath in a retracted position relative to an outer sheath.

Referring now to FIGS. 8A and 8B, in yet another exemplary embodiment, in yet another exemplary embodiment, an outer sheath 7100, an inner sheath 7200, and a cap 7306 are provided which are similar to the outer sheath 3100, inner sheath 3200, and cap 3306 described above with respect to FIGS. 4A and 4B with similar components bearing similar reference numerals but advanced into the 7000s. Specifically, a slit 7140 is defined between a first extension member 7300 and a second extension member 7400 which is shorter than the first extension member 7300. In the embodiment shown in FIGS. 8A and 8B, in addition to the cap 7306 being operably connected to the first extension member 7300 with a hinge 7304 as discussed above, the first extension member 7300 is operably connected to the outer sheath 7100 with another hinge (functional hinge) 7303 which allows the first extension member 7300 to deflect, or pivot, relative to the outer sheath 7100. Likewise, the second extension member 7400 is operably connected to the outer sheath 7100 with another hinge (functional hinge) 7403 which allows the second extension member 7400 to deflect, or pivot, relative to the outer sheath 7100.

According to this embodiment, as the inner sheath 7200 is advanced and begins to curve, it is contemplate that both the first extension member 7300 and the second extension member 7400 deflect relative to the outer sheath 7100, such that the first extension member 7300 and the second extension member 7400 each extend at vectors different from the vector of the outer sheath 7100. Although the second extension member 7400 is depicted as shorter than the first extension member 7300, it is envisioned that the second extension member 7400 could be the same length as the first extension member 7300, or absent, similar to the other previously described embodiments.

Additional features may also be incorporated into one or more of the embodiments discussed above. For example, an elastic membrane or band may be incorporated to ensure that the outer sheath and/or the extensions return to the original shape when the inner sheath is fully retracted. Likewise, a third sheath (i.e., a tri-axial system) may be incorporated which surrounds the outer sheath of the embodiments shown and described above. Such a third outermost sheath can be an intact cylinder, which, upon retracting the two inner sheaths, would return the system to substantially cylindrical shape.

Figure 9:
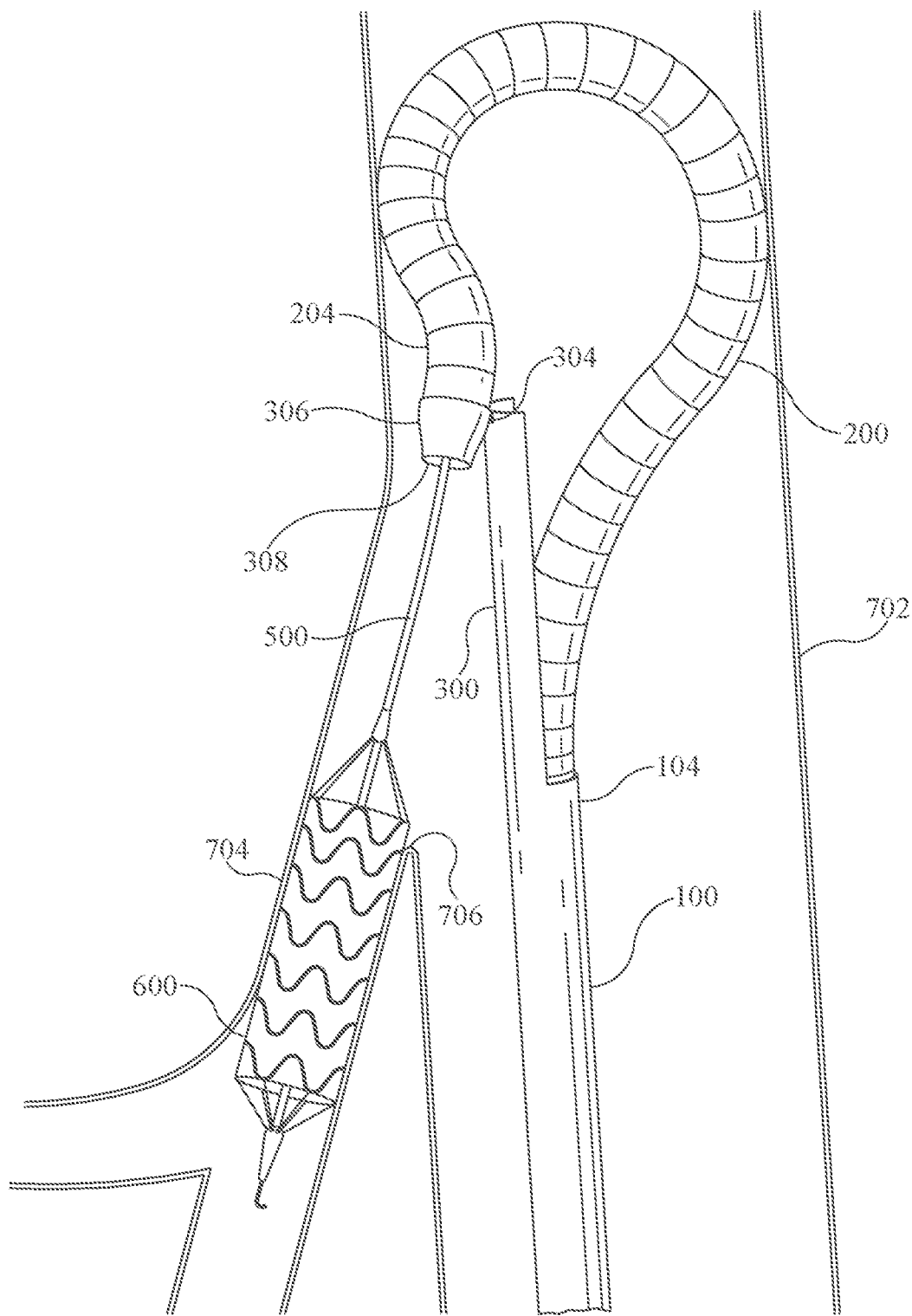
FIG. 9 depicts one exemplary guiding sheath system of present invention in use within the vasculature of a patient.

Referring once again to FIGS. 1A-1C but now also to FIG. 9, in one exemplary implementation of the methods of the present invention, an endovascular device, such as a stent, is delivered to a predetermined location in the vasculature of the patient. According to the methods of the present invention, an exemplary guiding sheath system, such as the system described above with respect to FIGS. 1A-1C, is first provided. Initially, the inner sheath 200 is positioned adjacent to the extension member 300, substantially as shown in FIG. 1A, with the distal end 204 of the inner sheath 200 directed in a vector that is substantially the same as the vector of the remainder of the inner sheath 200 (i.e., the portion of the inner sheath 200 still positioned within the outer sheath 100).

Next, the outer sheath 100 containing the inner sheath 200 is inserted into the vasculature of a patient. For example, an arteriotomy can be used to access a patient's femoral artery. The sheaths 100, 200 are placed in communication with the interior of the femoral artery with the use of a dilator and the sheaths 100, 200 are collectively advanced through the patient's vasculature until the cap 306 is positioned at a predetermined location within the vasculature. As previously mentioned, the cap 306 provides rounded leading edge which facilitates in the process of inserting and advancing the system through the vasculature. Of course, the outer sheath 100 is inserted such that the distal end 104 of the outer sheath 100 is maintained extracorporeal at all times.

As shown in FIG. 9, once the cap 306 is positioned at a predetermined location within the vasculature (i.e., within a primary vessel 702 adjacent to the opening 706 to a branching vessel 704), the inner sheath 200 is advanced relative to the outer sheath 100, such that the cap 306 and the distal end 204 of the inner sheath 200 is at a vector different than the vector of the distal end 104 of the outer sheath 100. In particular, the distal end 204 of the inner sheath 200 is positioned so that the opening 308 in the cap 306 is pointing towards the opening 706 to the branching vessel 704 while the distal end 104 of the outer sheath 100 is substantially aligned with the primary vessel 702. If necessary, the guiding sheath system is rotated within the primary vessel to orient the opening 308 of the cap 306 towards the branching vessel. To this end, the extension member 300 and hinge 304, or hinge-like connections, preferably have a sufficient width and rigidity to allow rotation of the system about the main axis of the outer sheath 100, even when the inner sheath 200 is extended, so as position the opening 308 in the cap 306 in line with a targeted branching vasculature.

Once the opening 308 in the cap 306 is pointing towards the opening 706 to the branching vessel 704, a guidewire 500 and endovascular device, here in the form of a stent 600, are inserted through the inner sheath 200 before exiting through the opening 308 in the cap 306. The distal end 204 of the inner sheath 200 directs the guidewire 500 forward along the vector of the distal end 204 of the inner sheath 200, towards, and into the branching vessel 704. The guidewire then directs the stent 600 into position forward of the distal end 204 of the inner sheath 200 along the vector of the distal end 204 of the inner sheath 200, where it is deployed within the branching vessel 704, as shown in FIG. 9.

The hinge 304 and cap 306 firmly maintains the position of the distal end 204 of the inner sheath 200 relative to the distal end 104 of the outer sheath 100, even as the curved portion of the inner sheath 200 changes shape during use. Specifically, in the case where a particularly rigid endovascular device is advanced through the inner sheath 200, the curved portion of the inner sheath 200 can flex and/or be adjusted manually, to successfully direct the endovascular device around the curve, while still maintaining the opening 308 in the cap 306 in the desired orientation and position. This, in turn, facilitates in the delivery of endovascular devices in angulated anatomy, such as the branching vessel 704 illustrated in FIG. 9.

Of course, it should be readily understood that the other exemplary systems shown in FIGS. 2A-2D, 3A-3C, 4, 5A-5B, 6A-6B, 7A-7B, and 8A-8B are each used in substantially the same manner as the system described above with respect to FIGS. 1A-1C. Furthermore, this is merely one exemplary use of the system of the present invention and variations may be made without departing from the spirit or scope of the present invention.

One of ordinary skill in the art will recognize that additional embodiments are possible without departing from the teachings of the present invention. This detailed description, and particularly the specific details of the exemplary embodiments disclosed therein, is given primarily for clarity of understanding, and no unnecessary limitations are to be understood therefrom, for modifications will become obvious to those skilled in the art upon reading this disclosure and may be made without departing from the spirit or scope of the present invention.

What is claimed is:

1. A guiding sheath system, comprising:
    a first sheath having a proximal end and a distal end;
    an extension member connected to the distal end of the first sheath, the extension member terminating in a distal end;
    a second sheath extending through the first sheath, the second sheath having a proximal end and a distal end;
    a cap connected to the distal end of the second sheath; and
    a hinge pivotally connecting the cap to the distal end of the extension member;
    wherein the first sheath, the extension member, the cap, and the hinge are made of the same material; and
    wherein, upon advancing the second sheath through the first sheath, the cap restrains the distal end of the second sheath and the cap deflects relative to the first sheath thereby causing a portion of the second sheath protruding from the first sheath to bend into a curve with the distal end of the second sheath at a vector different from a vector of the first sheath.

2. The guiding sheath system of claim 1, wherein the extension member is fixedly connected to the distal end of the first sheath with the extension member extending away from the distal end of the first sheath at a vector the same as the vector of the first sheath.

3. The guiding sheath system of claim 1, wherein the extension member is configured to deflect relative to the first sheath, such that, upon advancing the second sheath through the first sheath, the extension member extends at a vector different from the vector of the first sheath.

4. The guiding sheath system of claim 1, wherein the first sheath, the extension member, and the cap are formed from a unitary cylindrical sheath.

5. A method of delivering an endovascular device within the vasculature of a patient, comprising:
    providing a guiding sheath system including
        a first sheath having a proximal end and a distal end,
        an extension member connected to the distal end of the first sheath, the extension member terminating in a distal end,
        a second sheath extending through the first sheath, the second sheath having a proximal end and a distal end,
        a cap connected to the distal end of the second sheath, and
        a hinge pivotally connecting the cap to the distal end of the extension member,
        wherein the first sheath, the extension member, the cap, and the hinge are made of the same material;
    inserting the guiding sheath system within the vasculature of a patient such that the cap is at a predetermined location within the vasculature;
    advancing the second sheath through the first sheath such that the cap restrains the distal end of the second sheath and the cap deflects relative to the first sheath thereby causing a portion of the second sheath protruding from the first sheath to bend into a curve with the distal end of the second sheath at a vector different from a vector of the first sheath; and
    advancing an endovascular device through the second sheath to a position forward of the distal end of the second sheath along the vector of the distal end of the second sheath.

6. The method of claim 5, wherein the step of providing the guiding sheath system includes:
    providing a cylindrical sheath;
    cutting away a portion of the cylindrical sheath to form the extension member at the distal end of the sheath; and
    cutting partially around the distal end of the extension member to form the cap and hinge.

* * * * *